United States Patent [19]
Siegal

[11] Patent Number: 5,160,699
[45] Date of Patent: Nov. 3, 1992

[54] GERMICIDAL APPARATUS

[75] Inventor: Burton L. Siegal, Skokie, Ill.

[73] Assignee: Sellstrom Manufacturing Company, Palatine, Ill.

[21] Appl. No.: 649,856

[22] Filed: Feb. 1, 1991

[51] Int. Cl.⁵ .............................................. A61L 2/00
[52] U.S. Cl. ...................................... 422/24; 312/209
[58] Field of Search ........................ 422/186.3, 20, 24; 204/157.15; 312/209

[56]  References Cited
U.S. PATENT DOCUMENTS 3,683,638  8/1972  Devon ................................... 62/264
3,776,694 12/1973  Leittl ................................. 21/102 R
3,914,648 10/1975  Friedman et al. ............... 315/241 P
4,383,202  5/1983  Beck et al. ...................... 315/200 A
4,698,206 10/1987  Nevin ................................... 422/24

OTHER PUBLICATIONS

Lab Safety Supply Catalog, p. 142.
Global Occupational Safety Catalog, p. 28 Prior to 1990.

Primary Examiner—Brooks H. Hunt
Assistant Examiner—Daniel J. Jenkins
Attorney, Agent, or Firm—Richard A. Speer

[57]  ABSTRACT

An enclosed sanitizing cabinet for exposing eyewear articles to ultraviolet radiation from a fluorescent ultraviolet lamp which preferably extends substantially the entire height of the cabinet. The cabinet contains shelf-forming rod members spaced and configured to support eyewear articles in such manner that the surfaces of said articles which contact a user's skin in use are exposed to ultraviolet radiation. Interior surfaces of the cabinet are of a nature and formed of materials so as to reflect ultraviolet radiation to all articles therein and to minimize the differential in radiation exposure between articles adjacent and more remote from the radiation source.

10 Claims, 3 Drawing Sheets

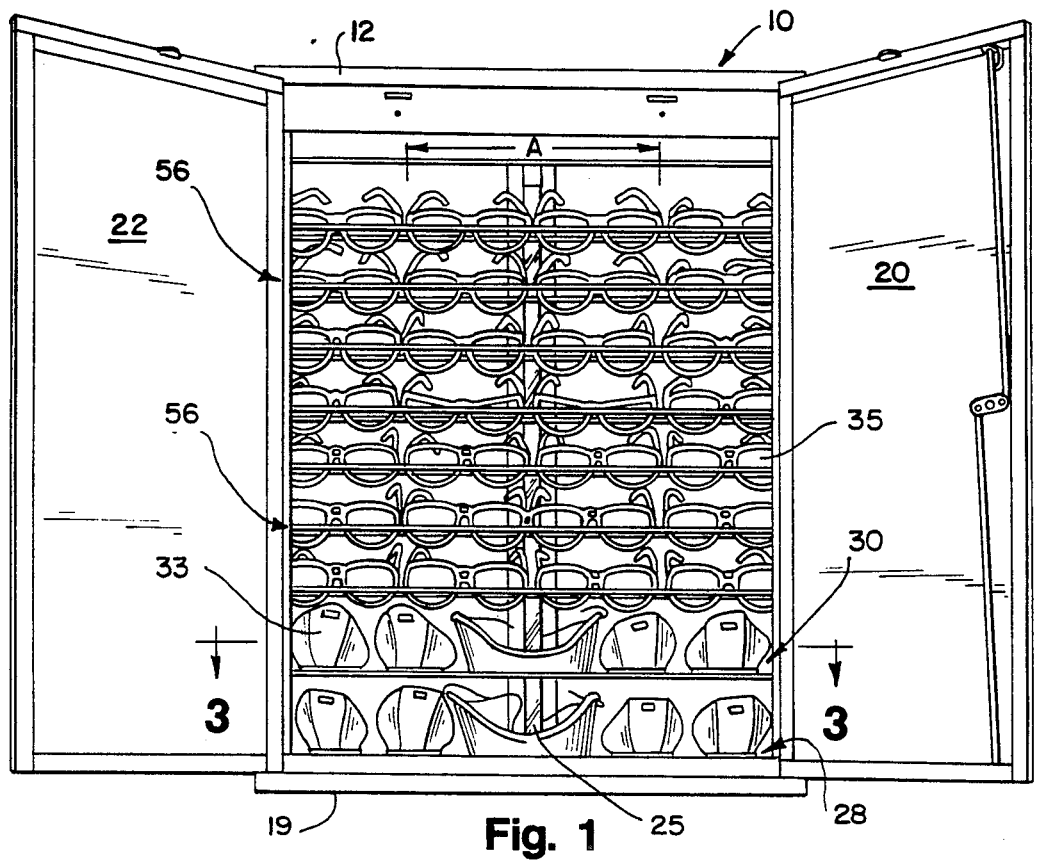
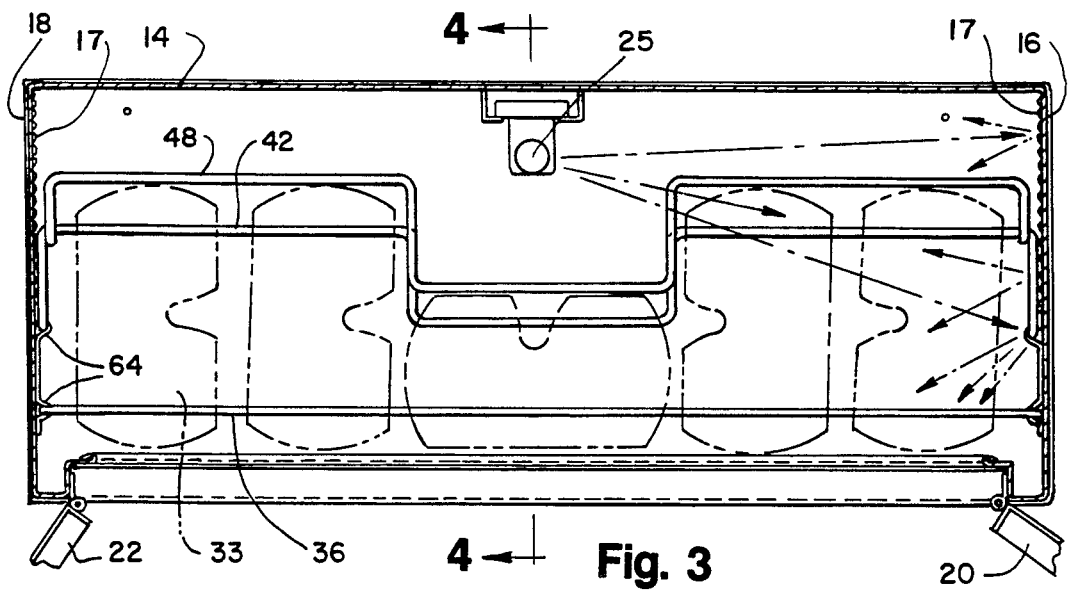

GERMICIDAL APPARATUS

This invention relates to germicidal apparatus and more particularly to apparatus for killing by ultraviolet radiation bacteria on devices which come into contact with human skin and still more particularly to apparatus for killing bacteria on protective devices worn on the face, such as protective eye glasses and goggles.

BACKGROUND OF THE INVENTION

Germicidal cabinets are used to reduce the bacterial population on articles such as protective glasses and goggles used by a number of people who share their use, such as in school shop and chemistry classes. In such situations, the protective articles are returned to the germicidal cabinet at the end of one class, exposed to ultra-violet radiation for a time so as to be ready for use when the next class begins.

Protective eye glasses and goggles are usually formed of a plastic material and accordingly "sanitizing" of such articles must be conducted under conditions so as not to adversely affect the article, particularly the impact strength thereof. Indeed, serious reduction in impact strength of such articles may result in greater danger to the user than the bacteria carried by the articles. Moreover, it is highly desirable that sanitizing of such articles be accomplished in a short period of time with a high degree of bacterial kill. Effective sanitizing generally means that 99% or more of the bacteria population are killed. Also, in school classes, for example, it is desirable that a number of protective eye glasses or goggles be sanitized simultaneously with short exposure to the ultraviolet radiation and in a manner that all surfaces of the article which come into contact with the skin of a user be effectively sanitized.

OBJECTS OF THE INVENTION

It is therefore a principal object of the invention to provide an advantageous apparatus for sanitizing articles such as protective eye glasses or goggles which come in contact with a user's skin.

It is a further object of the invention to provide an apparatus for effectively sanitizing protective eye glasses or goggles in short periods of time with relatively low levels of ultraviolet radiation.

It is another object of the invention to provide an apparatus for sanitizing protective eye glasses or goggles in which a plurality of such devices can be effectively and uniformly sanitized in a short period of time.

It is another object of the invention to provide apparatus for sanitizing eyewear articles by exposure to ultraviolet radiation in which the differential in exposure of articles adjacent to and remote from the source of ultraviolet radiation is minimized.

It is still another object of the invention to provide germicidal apparatus utilizing an ultraviolet radiating lamp in which the output of the lamp remains consistent over a long life.

SUMMARY OF THE INVENTION

The present invention provides an enclosed germicidal cabinet having a top, bottom, rear and side walls and a front door which opens for access thereto. A germicidal lamp which emits ultraviolet radiation at a germicidal frequency is positioned vertically within the cabinet, preferably mid-way between the sides thereof. A plurality of horizontally extending rod members are arranged within the cabinet for supporting articles to be exposed to ultraviolet radiation. Interior surfaces of the cabinet are of such nature and formed of materials which reflect ultraviolet radiation so that all articles positioned within the cabinet are exposed to the radiation and the differential in exposure between articles adjacent and more remote from the source of radiation is minimized. The germicidal cabinet is provided with horizontally extending rod members which form shelves to support either protective eye glasses or goggles or a combination thereof in such manner that the ultraviolet radiation contacts the inner surfaces of such articles which come into contact with a user's skin. The shelf-forming rod members are spaced and configured so as to insure that the eyewear articles are positioned for adequate exposure of the skin-contacting surfaces thereof to the radiation.

According to a particularly preferred embodiment, a germicidal fluorescent ultraviolet lamp of sufficient length is employed to extend substantially the entire interior height of the cabinet. A fluorescent ultraviolet lamp of greater length than is normally employed in prior art germicidal cabinets insures more uniform distribution of the radiation and permits operation of the lamp at reduced power levels. A flasher-type circuit is employed for operation of the ultraviolet lamp whereby the lamp is constantly maintained warm permitting continuous on-off cycling of the lamp.

DESCRIPTION OF THE DRAWINGS

The advantages of the invention will be apparent from the following detailed description of illustrative embodiments in conjunction with the accompanying drawings wherein:

FIG. 1 is a front perspective view of a preferred embodiment of a germicidal cabinet in accordance with the invention showing a plurality of eye glasses and goggles positioned therein.

FIG. 3 is a sectional view taken along line 3—3 of FIG. 1.

Figure 2:
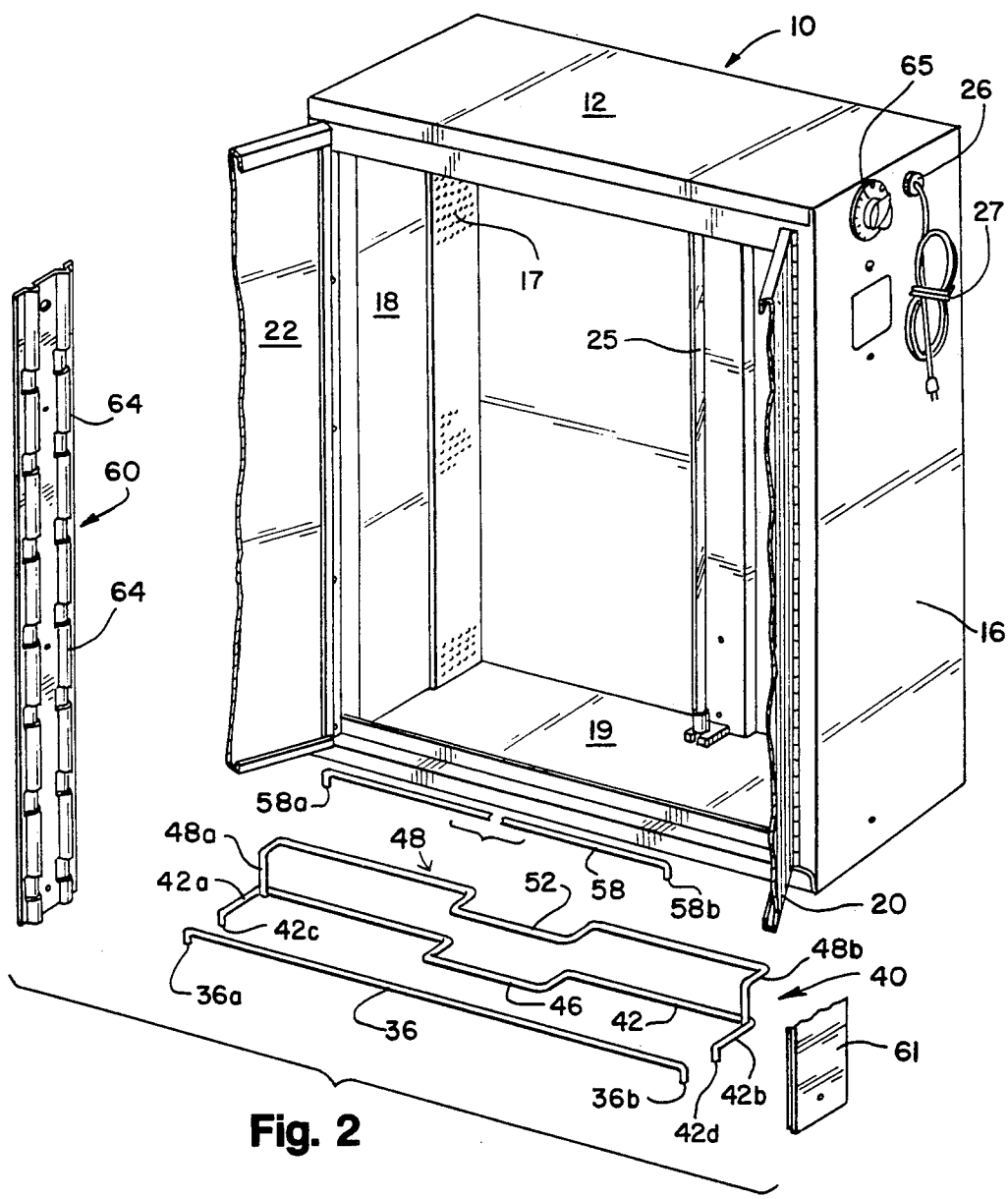
FIG. 2 is a partially exploded perspective view of the cabinet of FIG. 1 with the doors broken away and showing typical rods which when assembled form shelves for eye glasses and goggles.

Referring to the drawings, numeral 10 designates one embodiment of a germicidal cabinet in accordance with the invention. The cabinet 10 is of metal construction having a top 12, a back wall 14, opposed side walls 16 and 18 and bottom 19. Access front doors 20 and 22 are hingedly connected to provide access to the interior of the cabinet, although a single access door can also be employed as a matter of preference.

Centrally mounted adjacent the back wall is a germicidal lamp 25 which emits ultra-violet radiation. Such germicidal lamps having a quartz tube peaked to emit ultraviolet radiation at germicidal frequency are commercially available. One supplier for such germicidal lamps is, for example, Light Sources, Inc., Milford, Conn.

The germicidal ultraviolet lamp 25 is mounted vertically in the cabinet 10, preferably adjacent to but spaced from the rear wall 14. The lamp is of sufficient length to extend substantially the entire height of the interior of cabinet 10. For example, if the interior height of the cabinet is 32 inches, a germicidal lamp of approximately 31 inches is preferred. The cabinet is provided with an opening 26 to permit the lamp to be connected to a source of electrical energy by means of line cord 27.

Protective eye glasses or goggles made of plastic can be quite opaque to ultraviolet radiation which for germicidal purposes is peaked at a wave length of 2537 Angstroms. Accordingly, it is very important that the protective eyewear articles be positioned within the germicidal cabinet so as to expose to ultraviolet radiation those portions of the articles where pathogenic skin contaminants are most likely to be contacted, such as around the ears, brow, nose and upper cheeks. To this end, the germicidal cabinet of the invention is provided with horizontally extending rack or shelf members which hold the protective eye pieces in a position so that the germicidal ultraviolet radiation strikes the parts of the eyewear article which come into contact with a user's skin.

FIG. 1 of the drawings shows one preferred form of germicidal cabinet for sanitizing both eye glasses and goggles. Two racks or shelves 28 and 30 for goggles 33 are provided in the illustrative cabinet shown in FIG. 1. As shown more particularly in FIG. 2, each of the shelves 28 and 30 are formed by a horizontally extending front bar 36 having downwardly turned distal end portions 36a and 36b. The goggle shelves are completed by a two-tiered frame 40 having a horizontally extending lower support rod 42 having forwardly extending side arms 42a and 42b which terminate in downwardly turned end portions 42c and 42d, respectively. The lower support rod 42 is formed with a U-shaped center portion 46 which is of a size to accommodate a protective eye goggle as shown in FIGS. 1 and 3. Secured to the lower support rod 42 and extending upwardly therefrom is a guide barrier rod 48. The barrier rod serves to maintain the goggles in proper position during sanitizing. The barrier rod 48 has a shape complementary to the support rod 42 and is formed with forwardly and downwardly projecting end portions 48a and 48b which are joined to the support bar 42. The barrier rod 48 is formed with a U-shaped center portion 52 complementary to the center portion of rod 48.

With a goggle shelf formed with front support rod 36 and the two-tiered frame 40 as illustrated, five eye goggles can be placed on one shelf with one goggle being positioned in the center of the shelf, face down, parallel to the rear wall of the cabinet, and two pair of goggles placed face down parallel to the side walls of the cabinet on each side of the center goggle. This arrangement insures that ultra-violet radiation contacts the interior surfaces of goggles which come into contact with a user's skin.

Figure 4:
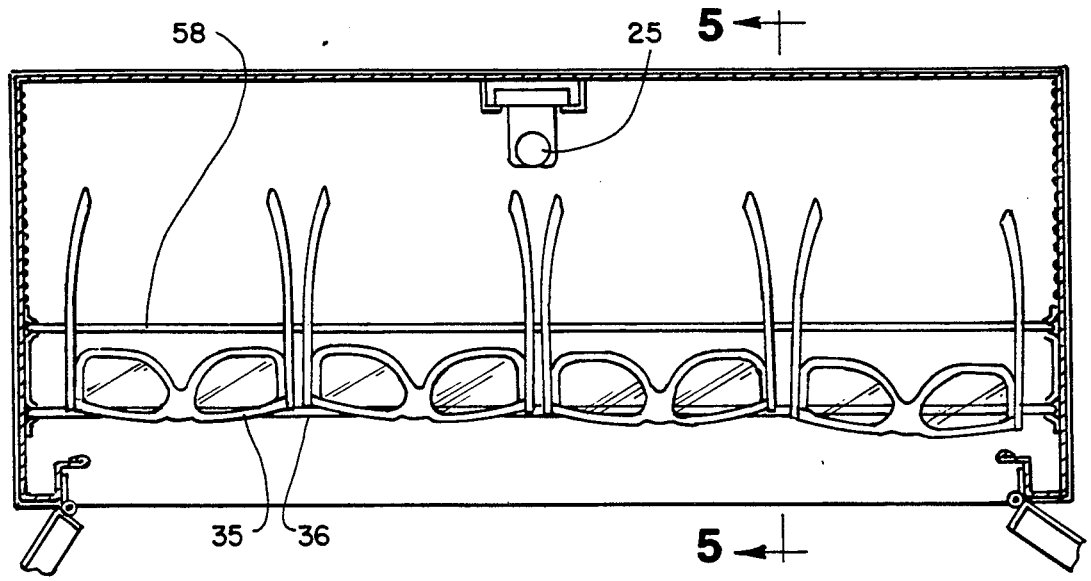
FIG. 4 is a partial plan view showing the positioning of protective eye glasses for exposure to ultraviolet radiation.
Figure 5:
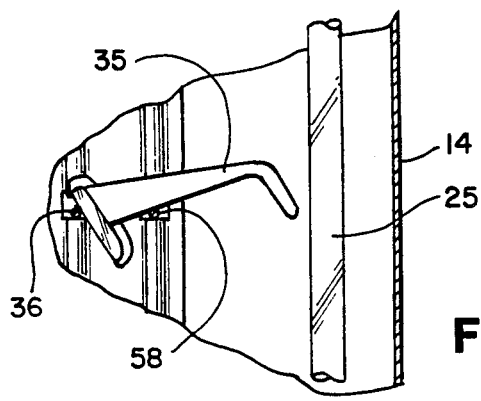
FIG. 5 is a schematic side view taken along the line 5—5 of FIG. 4 showing eye glasses suspended on the shelf-forming rod members in position to receive germicidal radiation.

The preferred embodiment of germicidal cabinet illustrated in FIG. 1 is adapted for sanitizing two rows of goggles 33 and seven rows of eye glasses 35. The eye glasses 35 are supported on a shelf in a manner that the eye glasses can be fully open as illustrated in FIGS. 4 and 5. The eye glass shelves 56 for eye glasses are formed from two spaced horizontally extending rods, namely a front rod 36 and a rear rod 58. The rear rod 58 has downwardly extending end portions 58a and 58b. As seen particularly in FIG. 5, the eye glasses must be opened and not folded so as to be supported by the horizontally extending racks 36 and 58.

To retain the goggle shelves and eye glass shelves in horizontal position within the germicidal cabinet, two hanger strips 60 and 61 are secured on each interior side of the cabinet. The hanger strips are provided with a plurality of open ended tubular receptors 64 which receive the downwardly projecting end portions of the shelf rods 36, 42 and 58, as the case may be. The tubular receptors are vertically spaced to provide the proper spacing for the goggle shelves or the eye glass shelves as is necessary. It will be apparent that the germicidal cabinet of this invention can be readily adapted to sanitize eye glasses or goggles, or a combination thereof. This is accomplished simply by using the proper combination of support rods to form either an eye glass shelf or a goggle shelf.

For simultaneously sanitizing a plurality of protective eyewear articles, it is important that the germicidal ultraviolet radiation be spread uniformly throughout the cabinet so that protective articles close to the ultraviolet lamp are not over-exposed to the radiation while insuring that the articles remote from the lamp receive adequate exposure to the radiation. Thus, the germicidal cabinet of this invention is constructed so as to reduce the reflectivity of the germicidal lamp in areas adjacent the lamp and to increase reflectivity behind articles more remote therefrom. Accordingly, the central portion, designated area A, of the rear wall 14 of the cabinet is covered with a material having a low degree of reflectivity, say a reflectivity of not more than 20% of the ultraviolet radiation. A suitable covering material for this purpose is white gloss paint having resistance to discoloration and/or loss of gloss when subjected to ultraviolet radiation. Other similar reflective surfaces can also be utilized.

Also, the interior top wall of the cabinet which contains the electrical circuitry is covered with a material which is highly reflective of the ultraviolet radiation, say a material which reflects greater than 80% of the ultraviolet radiation. Such materials include, for example, specular aluminum or non-specular aluminum. Similarly, both of the interiors of walls 16 and 18 of the cabinet are covered with a highly reflective material, preferably a material which reflects greater than 80% of the ultraviolet radiation, having an embossed surface which includes protuberances 17 so as to angularly reflect the ultraviolet radiation impinging thereon. The embossed interior surface of the side walls causes the ultraviolet radiation to be reflected downwardly so as to contact recesses of the outermost goggles and the shadowed recesses of goggles closer to the germicidal lamp.

The size of the germicidal cabinet can be varied As exemplary, the preferred cabinet illustrated in FIG. 1 has interior dimensions of 24¼ inches in width, 9¼ inches in depth and 32 inches in height. A cabinet of these dimensions permits either four eye glasses or five goggles to be positioned on one horizontal shelf for sanitizing. With this arrangement, no eye glass or goggle is more than one unit distant from the source of ultraviolet radiation, which is a preferred desideratum.

The construction of the new germicidal cabinet is such that eye glasses and/or goggles are supported in a position such that the protective eye articles must necessarily be fully open with the interior bacteria-carrying portions exposed to the source of ultraviolet radiation. By means of the hanger strips 60 and 61 the vertical spacing of the rod members forming the shelves can be varied. Generally a vertical space between goggle shelves of about 3⅞ inches and a vertical space of about 2¾ inches for eye glass shelves is eminently satisfactory.

As previously indicated, it is preferred that the germicidal lamp extend vertically a distance substantially equal to the interior height of the cabinet. Thus, in the preferred cabinet of FIG. 1, the interior height of the cabinet is 32 inches and the length of the germicidal lamp 25 is approximately 31 inches. In prior art germicidal cabinets, the length of the germicidal lamp employed is the standard one of 17 inches. The use of a longer germicidal lamp provides significant advantages in operation including reduced ultraviolet power requirements. Thus, I have found it possible to achieve effective sanitizing using a customized 31 inch long germicidal lamp at a 12 watt input or 0.40 watts per lamp inch as compared with 0.88 watts per inch of the standard 17 inch, 15 watt germicidal lamp.

Use of a longer lamp in combination with other features of my germicidal cabinet provides effective sanitizing within a period of about 5 minutes as compared to 15 minute periods required with prior art cabinets. Germicidal lamps of extra length as well as a ballast suitable to provide the required power output can be custom supplied from commercial suppliers.

It is particularly preferred to utilize a flasher-type circuit with the germicidal cabinet of this invention for operation of the ultraviolet lamp. Flasher-type circuits are sometimes used in connection with flashing fluorescent signs but are not used with germicidal or sanitizing cabinets as far as is known. Flasher-type circuits employ a ballast that maintains a low voltage in the lamp filaments at all times that electric power is available and when the lamp is started a high starting voltage is applied that decays into a running voltage. Operation of the lamp by a flasher-type circuit keeps the lamp filaments warm, thereby permitting continuous on-off cycling of the lamp.

Experience has shown that with prior art germicidal cabinets subjected to six use cycles per day, the rated cold start life of the ultraviolet lamp used therein is exhausted in about two years and with the lamp output dropping considerably long prior to failure. In contrast, by using a flasher-type circuit to operate the ultraviolet lamp, virtually an unlimited number of cycles can be achieved and by virtue of the burn time being only about 5 minutes (⅓ of prior art germicidal lamps) the lamps rated life is in excess of 20 years.

It is to be understood that a single access door can be used in the germicidal cabinet in lieu of double doors shown in the preferred embodiment of FIG. 1. Also, the access door or doors can be provided with concealed tamper resistant interlock switches as is known so that electrical power to the lamp is shut off should the access door be inadvertently opened during operation of the unit. The unit can be, and preferably is, provided with a timer 65 for timed operation.

Figure 6:
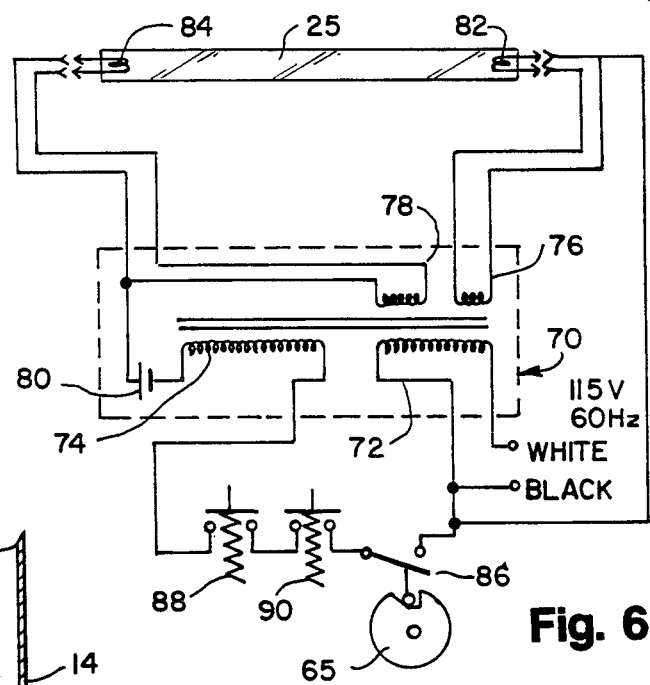
FIG. 6 is a preferred schematic diagram for operation of the ultraviolet germicidal cabinet.

FIG. 6 shows schematically a diagram for a flasher-type circuit for use in a preferred embodiment of this invention. Referring to FIG. 6, the timer 65 is coupled to a ballast 70. The ballast 70 includes a transformer having a primary 72, a high voltage secondary 74, a first and a second low voltage secondary 76 and 78 and a capacitor 80. The primary 72 is coupled to an A.C. line of 115 volts, 60 Hertz. The primary is used to develop the induced currents in each of the secondaries for operating the lamp 25.

The lamp 25 includes a first and a second filament 82 and 84 which are continuously energized by the first and second low voltage secondaries 76 and 78. By continuously delivering power to the filaments, continuous on-off cycling of the lamp is tolerated without reduction of its operating life.

The high voltage secondary 74 provides the energy to light the lamp. In series with the secondary 74 is the capacitor 80 which is used for reducing the power factor as would be understood by one skilled in the art. The capacitor 80 is coupled to one side of the lamp 25 and the other side of the secondary 74 is coupled to the remaining side of the lamp 25 through a plurality of interlock switches.

A timer switch 86 is used to cycle the lamp between the on and off conditions. Since the filaments 82 and 84 are continuously lit, the lamp 25 can be cycled on and off continuously, if desired. When the timer switch 86 closes, and the doors 20 and 22 are closed, high voltage is applied across the lamp, turning it on. When switch 86 opens, the lamp 25 is turned off. The length of the on-off cycle is controlled mechanically, in this instance, by a rotating wheel which rotates at a speed determined according to the sanitizing time period as would be understood by one skilled in the art. Alternatively, the switch 86 could be controlled by a solenoid coupled to an electronic timer.

A first and a second door interlock switch 88 and 90 are in circuit with the high voltage secondary 74. These two switches act as safety interlock switches for turning off the lamp 25 when either of the front doors 20 and 22 are opened. When either of the doors are opened, the appropriate door interlock switch opens the circuit of the high voltage secondary 74, thereby turning lamp 25 off.

The germicidal cabinet of the present invention involves a number of novel features which provide significant advantages. The cabinet of the invention affords excellent sanitizing action in short periods of time with minimum exposure of the plastic eyewear to the destructive effects of ultraviolet rays. The cabinet insures that the target bacteria are not shielded from the ultraviolet radiation, and the radiation level therein is maintained constant both vertically and horizontally. Moreover, the output level of the fluorescent ultraviolet lamp remains high over long periods of time eliminating the necessity of raising the initial output level to compensate for fall-off. With the novel germicidal cabinet efficient sanitizing action is achieved in one-third the time usually required with prior art germicidal cabinets and with lower ultraviolet power levels. The greatly extended life of the germicidal lamp is clearly a significant economic advantage. Effective distribution of the ultraviolet radiation throughout the cabinet eliminates overexposure of eyewear articles near the source of ultraviolet radiation. This minimizes the necessity of replacing many prematurely discolored and/or brittle eyewear articles such as protective eye glasses and goggles. This, of course, is an additional significant economic benefit.

Those modifications and equivalents which fall within the spirit of the invention are to be considered a part thereof.

What is claimed is:

1. Apparatus for exposing protective eyewear to ultraviolet radiation comprising a cabinet including two first walls having preselected vertical and lateral dimensions, two second walls joined to and extending between said two first walls, the said second walls having a vertical dimension equivalent to that of said two first walls and a lateral dimension substantially less than the lateral dimension of said two first walls, means defining an access opening into said cabinet in one of said two first walls, reflector means on each interior surface of said second walls having a textured surface that reflects ultraviolet radiation at a plurality of angles to provide a substantially uniform level of radiation exposure to eyewear throughout the cabinet, a single lamp having a length substantially equal to the vertical dimension of the said two first walls disposed on one of said first walls substantially at the center thereof which lamp emits ultraviolet radiation at a germicidal frequency, and support means within said cabinet configured so as to cradle and support protective eyewear.

2. Apparatus in accordance with claim 1 wherein said lamp is a fluorescent lamp operated in a circuit which maintains a low warming voltage on the lamp at all times when electrical power is available thereto.

3. Apparatus in accordance with claim 1 wherein the rows of shelves are configured so as to support one or more pieces of eyewear selected from eye glasses and eye goggles.

4. Apparatus in accordance with claim 1 wherein one or more rows of shelves within said cabinet are configured so as to cradle and support one or more pieces of protective eyewear in substantially fully opened position.

5. Apparatus in accordance with claim 1 wherein one or more shelves within said cabinet are configured so as to cradle and support one or more eye glasses in substantially fully opened position and one or more shelves within said cabinet are configured so as to cradle and support one or more eye goggles in substantially fully opened position.

6. Apparatus in accordance with claim 1 wherein a portion of the one of the said first walls on which said ultraviolet lamp is disposed has a surface which reflects not more than about 20% of impinging ultraviolet radiation.

7. Apparatus in accordance with claim 1 in which said reflector means are aluminum.

8. Apparatus in accordance with claim 1 in which said textured surface of said reflector means further comprises an embossed surface providing protuberances which extend in a direction away from said second wall into the cabinet.

9. Apparatus in accordance with claim 1 in which said two first walls comprise the front and rear walls of the cabinet.

10. Apparatus in accordance with claim 9 in which said lamp is disposed on said rear wall of the cabinet.

* * * * *